United States Patent
Komura et al.

(10) Patent No.: US 7,493,795 B2
(45) Date of Patent: Feb. 24, 2009

(54) GAS DETECTION METHOD AND GAS DETECTION APPARATUS

(75) Inventors: Hajime Komura, Osaka (JP); Kazuo Onaga, Osaka (JP); Mariko Sugimura, Hyogo (JP); Hiroshi Koda, Hyogo (JP); Kazuyasu Iida, Hyogo (JP)

(73) Assignee: Suntory Limited, Osaka-Shi (JP)

( * ) Notice: Subject to any disclaimer, the term of this patent is extended or adjusted under 35 U.S.C. 154(b) by 0 days.

(21) Appl. No.: 10/586,531

(22) PCT Filed: Jan. 19, 2005

(86) PCT No.: PCT/JP2005/000584

§ 371 (c)(1),
(2), (4) Date: May 4, 2007

(87) PCT Pub. No.: WO2005/068989

PCT Pub. Date: Jul. 28, 2005

(65) Prior Publication Data

US 2007/0277588 A1  Dec. 6, 2007

(30) Foreign Application Priority Data

Jan. 20, 2004  (JP) .............................. 2004-012037

(51) Int. Cl.
*G01N 30/64* (2006.01)

(52) U.S. Cl. .................... 73/19.02; 73/23.22; 73/23.35; 73/23.4; 422/89; 422/90

(58) Field of Classification Search ................ 73/31.05, 73/19.01, 19.02, 19.12, 23.22, 23.35, 23.39, 73/23.4, 23.41, 23.42; 422/83, 88, 89, 90
See application file for complete search history.

(56) References Cited

U.S. PATENT DOCUMENTS 4,535,620 A * 8/1985 Cunningham .............. 73/23.36

(Continued)

FOREIGN PATENT DOCUMENTS

EP  0 060 944 A  9/1982

(Continued)

OTHER PUBLICATIONS

European Search Report mailed Jan. 10, 2008 issued in EP Application No. 05 70 3821.

(Continued)

*Primary Examiner*—David A. Rogers
(74) *Attorney, Agent, or Firm*—Drinker Biddle & Reath LLP

(57) ABSTRACT

The present invention provides a gas detection method and detection apparatus that provide better sensitivity and faster recovery after response than conventional gas detection methods and apparatus, by improving on these conventional methods and apparatus. The present invention is a gas detection method, in which the target gas is detected while oxygen is supplied to a sensor element 11a of a metal oxide-type gas sensor 11, wherein the target gas is detected while water vapor is supplied to the sensor element 11a, and is also a gas detection apparatus equipped with an oxygen supply means 14 for supplying oxygen to a sensor element 11a of a metal oxide-type gas sensor 11, said gas detection apparatus being provided with a water vapor supply means 15 for supplying water vapor to the sensor element 11a.

7 Claims, 2 Drawing Sheets

U.S. PATENT DOCUMENTS

| | | | |
|---|---|---|---|
| 4,911,892 A | * | 3/1990 | Grace et al. .................... 422/94 |
| 5,602,326 A | * | 2/1997 | Takahashi et al. .......... 73/31.06 |
| 7,013,707 B2 | * | 3/2006 | Prohaska et al. ............. 73/23.4 |
| 7,153,272 B2 | * | 12/2006 | Talton ........................ 600/543 |

FOREIGN PATENT DOCUMENTS

| | | |
|---|---|---|
| EP | 0 731 351 A2 | 9/1996 |
| EP | 0 902 279 A1 | 3/1999 |
| EP | 0 903 576 A2 | 3/1999 |
| JP | 54-24095 | 2/1979 |
| JP | 10-179747 | 7/1998 |
| JP | 2001-13047 | 1/2001 |
| JP | 2001-013047 | 1/2001 |
| JP | 2001-165828 | 6/2001 |
| JP | 2003-42989 | 2/2003 |
| JP | 2003-47659 | 2/2003 |
| JP | 2003-57223 | 2/2003 |
| JP | 2003-75384 | 3/2003 |
| WO | 03/019169 A1 | 3/2003 |

OTHER PUBLICATIONS

Horrillo et al., "Influence of the deposition conditions of $SnO_2$ thin films by reactive sputtering on the sensitivity of urban pollutants", *Sensors and Actuators B* 45 (1997) pp. 193-198.

Skafidas et al., "Modelling and simulation of tin oxide based thick-film gas sensors using Monte Carlo techniques", *Sensors and Actuators B*, vol. B19, No. 1-3, part 2, Apr. 1994, pp. 724-728; (Abstract attached, Proceedings of the Eurosensors VII Conference, Budapest, Hungary, Sep. 26-29, 1993).

\* cited by examiner

GAS DETECTION METHOD AND GAS DETECTION APPARATUS

TECHNICAL FIELD

The present invention relates to a gas detection method in which the target gas is detected while oxygen is supplied to a sensor element of a metal oxide-type gas sensor, and to a gas detection apparatus equipped with a metal oxide-type gas sensor and an oxygen supply means for supplying oxygen to a sensor element of this metal oxide-type gas sensor.

BACKGROUND ART

A gas chromatograph that analyzes a target gas after separating it into a plurality of component gases is known, for example, as such a gas detection apparatus. A metal oxide-type gas sensor is also known as a sensor for quantitatively detecting the component gas that is to be analyzed. With this kind of metal oxide-type gas sensor, an oxygen supply means for supplying oxygen to the sensor element is provided for cleaning the sensor element of the gas sensor, and the component gas is detected while oxygen is supplied from the oxygen supply means to the sensor element (see Patent Document 1, for example).

Patent document 1: JP 2001-165828 A

DISCLOSURE OF INVENTION

Problem to be Solved by the Invention

The inventors conducted research aimed at improving the sensitivity and response of a metal oxide-type gas sensor such as that described in the above-mentioned patent document, and arrived at the present invention as the result of various and repeated experiments. Therefore, it is an object of the present invention to improve on conventional gas detection methods and apparatus and thereby provide a gas detection method and detection apparatus with better sensitivity and faster response than conventional gas detection methods and apparatus.

Means for Solving Problem

The first characteristic constitution of the present invention is a gas detection method in which the target gas is detected while oxygen is supplied to a sensor element of a metal oxide-type gas sensor, wherein the target gas is detected while water vapor is supplied to the sensor element.

With the first characteristic constitution of the present invention, the target gas is detected while water vapor is supplied to a metal oxide-type gas sensor in addition to oxygen being supplied to this sensor element, so, as will be clear from the experiment results discussed below, the recovery after response to the target gas is faster, and as a result sensitivity is also improved, making it possible to detect the target gas at better sensitivity and faster recovery than with conventional methods.

The second characteristic constitution of the present invention is the above-mentioned gas detection method, wherein the target gas is a component gas separated in a separation column.

With the second characteristic constitution of the present invention, since the target gas is a component gas that has been separated in a separation column, even when the target gas includes a plurality of component gases, the various component gases can be accurately detected with good sensitivity and fast response.

The third characteristic constitution of the present invention is a gas detection apparatus equipped with an oxygen supply means for supplying oxygen to a sensor element of a metal oxide-type gas sensor, provided with a water vapor supply means for supplying water vapor to the sensor element.

With the third characteristic constitution of the present invention, in addition to an oxygen supply means for supplying oxygen to a sensor element of a metal oxide-type gas sensor, there is also provided a water vapor supply means for supplying water vapor to this sensor element. This constitution affords faster response to the target gas, as will be clear from the experiment results discussed below. As a result, detection is possible with better sensitivity and faster recovery than with conventional apparatus.

The fourth characteristic constitution of the present invention is the above-mentioned gas detection apparatus, wherein humidified oxygen is obtained by using water vapor supplied from the water vapor supply means to humidify oxygen supplied from the oxygen supply means, and this humidified oxygen is supplied to the sensor element.

With the fourth characteristic constitution of the present invention, humidified oxygen is obtained by using water vapor supplied from the water vapor supply means to humidify oxygen supplied from the oxygen supply means. Since this humidified oxygen is supplied to the sensor element, the water vapor concentration can be kept stable more easily. It is also easier to maintain the ratio in which the water vapor and oxygen are supplied, and not only are the sensitivity and fast recovery after response to the target gas maintained even more reliably, but it is also possible to simplify the tubing system as compared to when the oxygen and water vapor are supplied by separate tubing systems, for example.

The fifth characteristic constitution of the present invention is the above-mentioned gas detection apparatus, wherein the humidified oxygen is obtained through oxygen supplied from the oxygen supply means into water used for producing water vapor and stored in the water vapor supply means.

With the fifth characteristic constitution of the present invention, since the humidified oxygen is obtained through oxygen supplied from the oxygen supply means into water used for producing water vapor and stored in the water vapor supply means, humidified oxygen can be reliably produced by an extremely simple and inexpensive constitution, which reduces the cost of the entire apparatus.

The sixth characteristic constitution of the present invention is the above-mentioned gas detection apparatus, wherein the relative humidity of the oxygen in the humidified oxygen is at least 40%.

With the sixth characteristic constitution of the present invention, since the relative humidity of the oxygen in the humidified oxygen is at least 40%, the required amounts of oxygen and water vapor are reliably supplied to the sensor element of the metal oxide-type gas sensor, and the desired fast response and good sensitivity can be reliably obtained.

The seventh characteristic constitution of the present invention is the above-mentioned gas detection apparatus, wherein the relative humidity of the oxygen in the humidified oxygen is from 40 to 80%.

With the seventh characteristic constitution of the present invention, since the relative humidity of the oxygen in the humidified oxygen is from 40 to 80%, the required amounts of oxygen and water vapor are reliably supplied to the sensor element of the metal oxide-type gas sensor, and the desired fast recovery and good sensitivity can be more reliably obtained.

The eighth characteristic constitution of the present invention is the above-mentioned gas detection apparatus, wherein the humidified oxygen is supplied to the sensor element at a substantially constant flow per unit of time during the gas detection operation performed by the metal oxide-type gas sensor.

With the eighth characteristic constitution of the present invention, since the humidified oxygen is supplied to the sensor element at a substantially constant flow per unit of time during the gas detection operation performed by the metal oxide-type gas sensor, the desired fast recovery and good sensitivity can be maintained during the gas detection operation, affording reliable detection.

The ninth characteristic constitution of the present invention is the above-mentioned gas detection apparatus, wherein the gas detection apparatus is equipped with a separation column for separating the target gas into a plurality of component gases, and the target gas detected by the metal oxide-type gas sensor is a component gas that has been separated by this separation column.

With the ninth characteristic constitution of the present invention, since the gas detection apparatus is equipped with a separation column for separating the target gas into a plurality of component gases, and the target gas detected by the metal oxide-type gas sensor is a component gas that has been separated by this separation column, even when the target gas includes a plurality of component gases, the various component gases can be accurately detected with good sensitivity and fast recovery.

The tenth characteristic constitution of the present invention is the above-mentioned gas detection apparatus, wherein the component gas and the humidified oxygen are supplied separately in substantially the same direction to the sensor element.

With the tenth characteristic constitution of the present invention, because the component gas and the humidified oxygen are supplied separately in substantially the same direction to the sensor element, unlike when the component gas and the humidified oxygen are supplied separately from different directions, for example, there is no dilution or dispersion of the component gas due to mixing of the component gas and the humidified oxygen. Therefore, the component gas can be more reliably detected by the sensor element.

BEST MODE FOR CARRYING OUT THE INVENTION

Embodiments of the gas detection method and detection apparatus pertaining to the present invention will be described through reference to the drawings.

As shown in FIG. 1, a gas chromatograph GC, which is an example of a gas detection apparatus, comprises a control unit 1, a sample injection component 2, a separation column 3, a detection component 4, a data processor 5, and so forth.

The gas chromatograph GC is also provided with a gas cylinder 6 for supplying a carrier gas CG. This gas cylinder 6 is filled with helium, $N_2$, or another such inert gas (with an oxygen content, as the partial pressure ratio, of 0.1% or less) as the carrier gas CG. The apparatus is designed so that the carrier gas CG is supplied from the gas cylinder 6 to the control unit 1 of the gas chromatograph GC.

The flow and pressure of the carrier gas CG supplied from the gas cylinder 6 are adjusted by the control unit 1 before the gas reaches the sample injection component 2. A sample S (the target gas) is vaporized by the sample injection component 2 and injected into the carrier gas CG, then transported by the carrier gas CG (mobile phase) to the separation column 3.

While the sample S in the carrier gas CG is moved through the separation column 3, it is separated into a plurality of component gases SG through interaction with the stationary phase, such as adsorption/desorption or two-phase partition. The various component gases SG thus separated are quantitatively detected by the detection component 4. The data processor 5 produces a gas chromatogram on the basis of these detection results.

As shown in FIG. 2, the detection component 4 is made up of a connecting portion 7, a reaction gas supply portion 8, and a sensor portion 9. In this embodiment, these three constituent portions 7, 8, and 9 are formed separately from each other but linked to each other by being fitted or threaded together. In another embodiment, these three constituent portions 7, 8, and 9 can be constituted integrally.

The connecting portion 7 is equipped with a through-hole 7a that passes through in the lengthwise direction. A capillary column 10 of the gas chromatograph GC that is inserted through this through-hole 7a goes through a supply chamber 8a of the reaction gas supply portion 8 and opens into a sensor chamber 9a of the sensor portion 9. Thus, the various component gases SG and the carrier gas CG that have passed through the separation column 3 are introduced directly into the sensor chamber 9a of the sensor portion 9.

A metal oxide-type semiconductor gas sensor 11 (the metal oxide-type gas sensor) is attached to the sensor portion 9, and a sensor element 11a of this semiconductor gas sensor 11 is disposed in the sensor chamber 9a in a state of being across from an opening in the capillary column 10.

A reaction gas introduction tube 12 is connected to the reaction gas supply portion 8. Humidified oxygen HO, that is oxygen gas that has been humidified by water vapor (as will be described in detail below), is introduced from this reaction gas introduction tube 12 into the supply chamber 8a, and then flows around the outer periphery of the capillary column 10 and to the sensor element 11a side. As a result, the component gases SG supplied from the capillary column 10 and the humidified oxygen HO supplied from the reaction gas introduction tube 12 are separately supplied in substantially the same direction to the sensor element 11a.

Thus, the component gases SG and the carrier gas CG supplied from the separation column 3 are supplied through the capillary column 10 to the sensor element 11a, and the humidified oxygen HO is supplied from outside the capillary column 10 to the sensor element 11a. As a result, the component gases SG are supplied to the sensor element 11a without being diluted by the humidified oxygen HO, and without being widely dispersed within the sensor chamber 9a.

Therefore, reliable detection is possible with the metal oxide-type semiconductor gas sensor 11. It is preferable here for the opening in the capillary column 10 to be moved as close as possible to the sensor element 11a, and for the gap between the two to be set to about 1 to 5 mm.

Furthermore, the capillary column 10 is disposed on the center line of the cylindrical sensor chamber 9a, and the sensor element 11a is disposed on this same center line. Therefore, after the component gases SG leaving the capillary column 10 are supplied to the sensor element 11a, they quickly leave the sensor element 11a, without standing near the sensor element 11a. This affords faster recovery after gas detection response.

The signal from the metal oxide-type semiconductor gas sensor 11, such as a change in the current or the electrical resistance, is processed by the data processor 5, and the above-mentioned gas chromatogram is produced.

The humidified oxygen HO is produced by a humidified oxygen generator 13, for example. This humidified oxygen generator 13 is made up of an oxygen supply means for supplying oxygen to the sensor element 11a, which is joined to a water vapor supply means for supplying water in a gaseous state (that is, water vapor) to the sensor element 11a.

The oxygen supply means is constituted by an oxygen supply tube 14 that supplies oxygen, or air containing oxygen. The water vapor supply means 15 is constituted by a container 16 that holds water W for producing water vapor and that is equipped with a heater (not shown), and a water vapor supply tube 17 that communicates with this container 16. A bubbler 14a attached to the distal end of the oxygen supply tube 14 is inserted into the water W used to produce water vapor, and generates air bubbles (the humidified oxygen HO) when the oxygen supplied from the oxygen supply tube 14 is discharged into the water via the bubbler 14a. This humidified oxygen HO is introduced into the supply chamber 8a via the water vapor supply tube 17 and the reaction gas introduction tube 12.

This humidified oxygen generator 13 produces, for example, humidified oxygen HO in which the relative humidity of the oxygen is at least 40%, and preferably from 40 to 80%. This humidified oxygen HO is set to be supplied to the sensor element 11a of the metal oxide-type semiconductor gas sensor 11 at a substantially constant flow per unit of time during at least the gas detection operation performed by the metal oxide-type semiconductor gas sensor 11.

However, the humidified oxygen HO does not necessarily have to be supplied to the sensor element 11a, and it is also possible to employ a configuration in which, for example, the oxygen supply tube 14 and the water vapor supply tube 17 are separately connected to the supply chamber 8a, and oxygen and water vapor are separately supplied to the sensor element 11a.

An actual gas analysis experiment was conducted using the gas chromatograph GC to confirm the effect of the present invention, and an experiment example and comparative example thereof will be discussed here.

The analysis experiment in the experiment example and comparative example was conducted in both cases at a room temperature of approximately 25° C., and more specifically, at a temperature of 20 to 30° C., and in the experiment example, the relative humidity of the oxygen in the humidified oxygen HO was set to a range of 40 to 80%.

In the experiment example and comparative example, a solution that contained about 5 ppm of each of seven components, namely, hexanol, isoamyl acetate, 2-octanone, trimethylpyrazine, limonene, 1-octanol, and dibutyl sulfide, was produced as the sample S. The solution (1 μL) was separated in a separation column with an inside diameter of 0.32 mm at a split ratio of approximately 1:7.

EXPERIMENT EXAMPLE

In the experiment example, in the analysis of the above-mentioned sample, the flow of the carrier gas CG was set to approximately 2 mL/minute, and the flow of humidified oxygen HO obtained by humidifying oxygen gas was set to approximately 10 mL/minute.

The results are given in FIG. 3, in which the vertical axis is the sensor output (microvolts: μV), and the horizontal axis is time (minutes).

COMPARATIVE EXAMPLE

In the comparative example, in the analysis of the above-mentioned sample, the flow of the carrier gas CG was set to approximately 2 mL/minute, just as in the experiment examples. However, the oxygen gas was not humidified, and analysis was conducted with the flow of unhumidified oxygen gas set to approximately 10 mL/minute.

The results are given in FIG. 4, in which the vertical axis is the sensor output (microvolts: μV), and the horizontal axis is time (minutes). The vertical and horizontal axes are both set to the same scale as in FIG. 3.

If we compare the fifth peak (limonene), for example, in the experimental example and comparative example, we see that the time from the start of detection to the end of detection is T1 in the experiment example, and T2 in the comparative example, and it is clear that T1 is shorter.

If the time from the start of detection to the end of detection is shorter, this means that the recovery after response will be correspondingly faster. In addition, this means that reliable detection will be possible even if there is a peak for another component gas immediately after the fifth peak, for example. Therefore, the results of the experiment example and comparative example confirm that supplying oxygen and water vapor to the sensor element of a metal oxide-type gas sensor greatly improves the response and sensitivity as compared to when just oxygen is supplied.

INDUSTRIAL APPLICABILITY

The present invention is equipped with a metal oxide-type gas sensor, and can be utilized in gas chromatography or the like in which a target gas is detected while oxygen is supplied to the sensor element of the metal oxide-type gas sensor.

Figure 1:
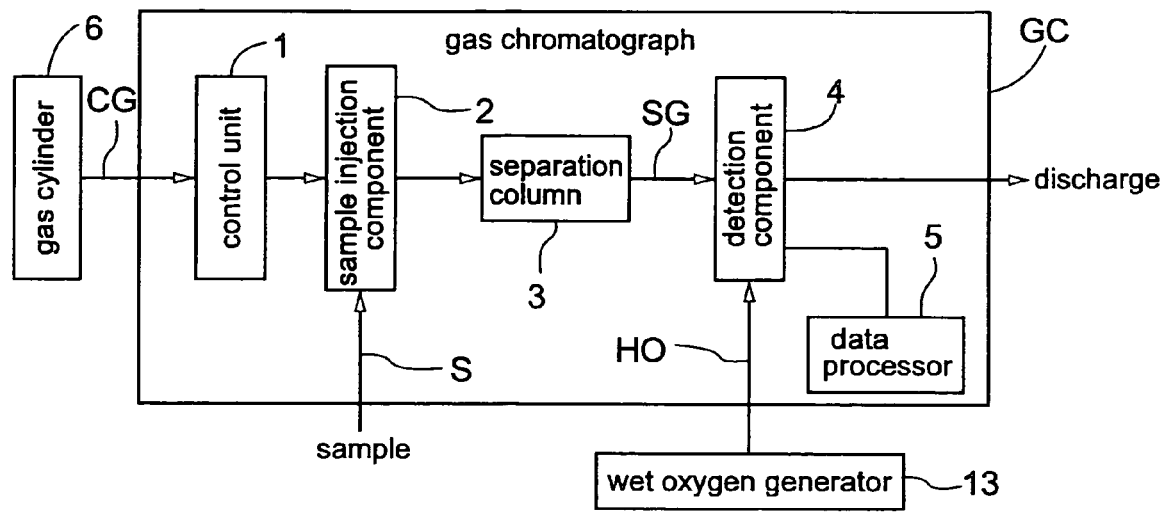
FIG. 1 is a diagram of the overall configuration of a gas detection apparatus.
Figure 2:
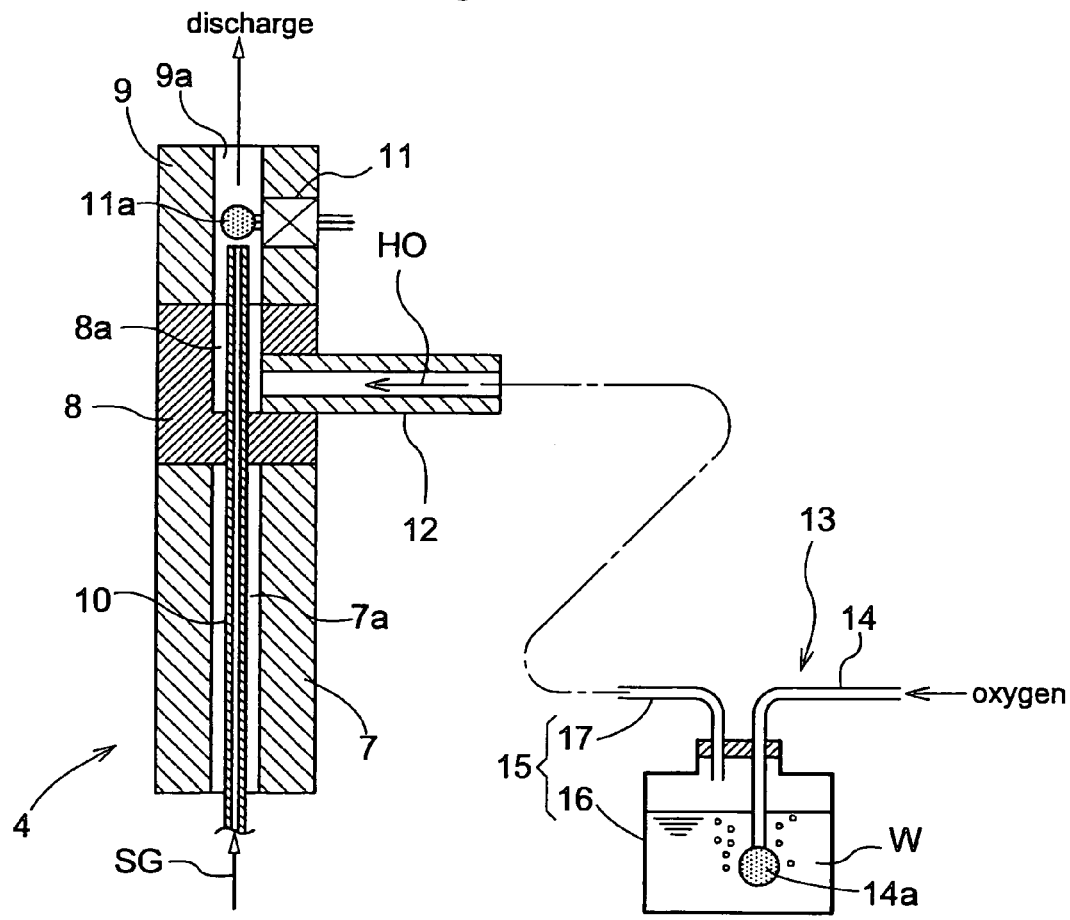
FIG. 2 is a diagram illustrating the detection component and humidified oxygen generator of the gas detection apparatus.
Figure 3:
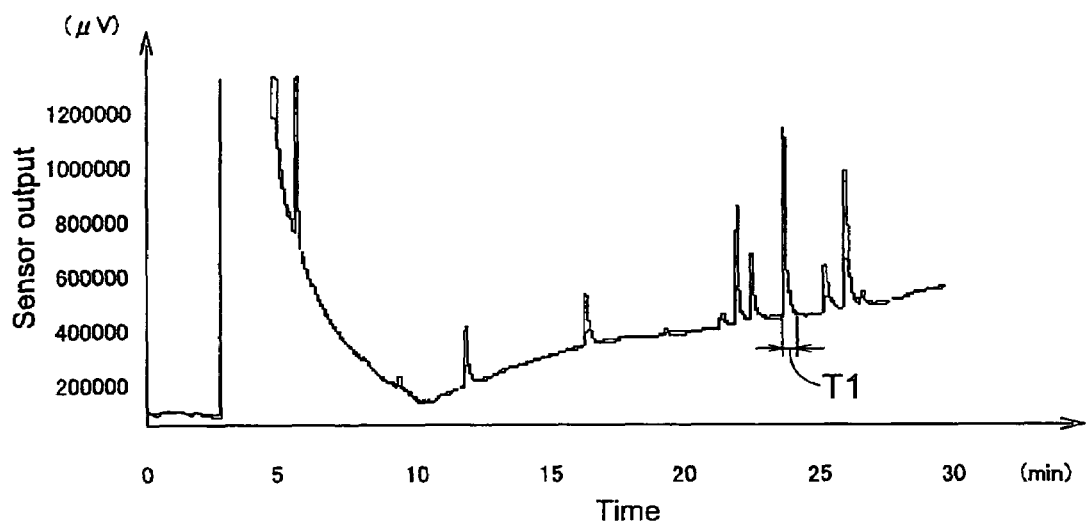
FIG. 3 is a graph of gas chromatography, showing the results of an experiment example.
Figure 4:
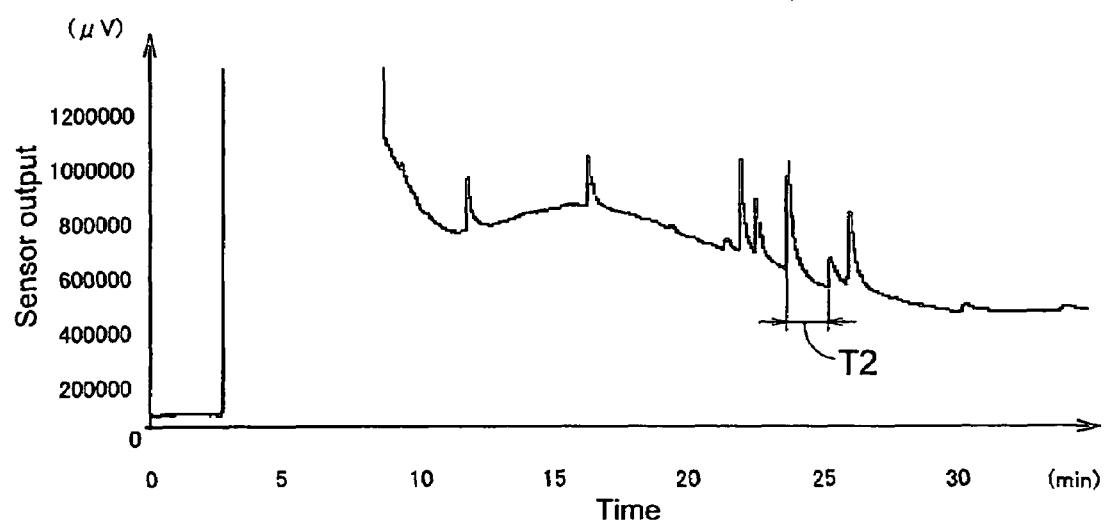
FIG. 4 is a graph of gas chromatography, showing the results of a comparative example.

Key
  3 separation column
  11 metal oxide-type semiconductor gas sensor
  11a sensor element
  14 oxygen supply means (oxygen supply tube)
  15 water vapor supply means
  GC gas detection apparatus
  SG component gas
  W water for producing water vapor
  HO humidified oxygen

The invention claimed is:
1. A gas detection apparatus equipped with an oxygen supply means for supplying oxygen to a sensor element of a metal oxide-type gas sensor,
    wherein said gas detection apparatus is provided with a water vapor supply means for supplying water vapor to the oxygen supplied by said oxygen supply means to provide humidified oxygen, and a separation column for separating said target gas into a plurality of component gases; and the target gas detected by the metal oxide-type gas sensor is a component gas that has been separated by this separation column.

2. The gas detection apparatus according to claim 1, wherein the humidified oxygen is obtained through oxygen supplied from the oxygen supply means into water used for producing water vapor and stored in the water vapor supply means.

3. The gas detection apparatus according to claim 1, wherein the relative humidity of the oxygen in the humidified oxygen is at least 40%.

4. The gas detection apparatus according to claim 1, wherein the relative humidity of the oxygen in the humidified oxygen is from 40 to 80%.

5. The gas detection apparatus according to claim 1, wherein the humidified oxygen is supplied to the sensor element at a substantially constant flow per unit of time during the gas detection operation performed by the metal oxide-type gas sensor.

6. A gas detection method, in which a target gas is detected while oxygen is supplied to a sensor element of a metal oxide-type gas sensor, wherein the target gas is detected as a component gas separated in a separation column while water vapor is supplied together with the oxygen to the sensor element.

7. The gas detection apparatus according to claim 1, wherein the component gas and the humidified oxygen are supplied separately in substantially the same direction to the sensor element.

* * * * *